US008050870B2

(12) United States Patent
Heckerman et al.

(10) Patent No.: US 8,050,870 B2
(45) Date of Patent: Nov. 1, 2011

(54) IDENTIFYING ASSOCIATIONS USING GRAPHICAL MODELS

(75) Inventors: David E. Heckerman, Bellevue, WA (US); Jonathan M. Carlson, Seattle, WA (US); Carl M. Kadie, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 1329 days.

(21) Appl. No.: 11/622,895

(22) Filed: Jan. 12, 2007

(65) Prior Publication Data

US 2008/0172209 A1    Jul. 17, 2008

(51) Int. Cl.
*G01N 33/48* (2006.01)
*G06F 19/14* (2006.01)
*G06F 19/00* (2011.01)

(52) U.S. Cl. .............................. 702/19; 706/13; 702/20
(58) Field of Classification Search .................. None
See application file for complete search history.

(56) References Cited

U.S. PATENT DOCUMENTS

| 6,564,151 | B1 | 5/2003 | Pellegrini et al. |
| 6,917,883 | B1 | 7/2005 | Ruddle et al. |
| 7,031,845 | B2 | 4/2006 | Scott et al. |
| 7,324,928 | B2 * | 1/2008 | Kitchen et al. ............ 703/3 |
| 2003/0220777 | A1 | 11/2003 | Kitchen et al. |
| 2004/0180376 | A1 | 9/2004 | Bader et al. |
| 2004/0219567 | A1 | 11/2004 | Califano et al. |
| 2004/0260664 | A1 | 12/2004 | Thiesson et al. |
| 2005/0086009 | A1 | 4/2005 | Hinds |
| 2006/0122816 | A1 | 6/2006 | Schadt et al. |
| 2006/0257888 | A1 | 11/2006 | Zabeau et al. |

OTHER PUBLICATIONS

Jojic et al., Efficient approximations for learning phylogenetic HMM models from data, Bioinformatics, vol. 20 (2004) pp. i161-i168.*
VijayaSatya, et al. "An Efficient Algorithm for Perfecting Phylogenetic Haplotyping," Proceedings of the 2005 IEEE Computational Systems Bioinformatics Conference.*
Cook et al., "Tree and spline based association analysis of gene-gene interaction models for ischemic stroke," Statistics of Medicine, vol. 23 (2004) pp. 1439-1453.*
Torgo et al., "Kernel regression trees, Proceedings of the poster papers of the European Conference on Machine Learning," 1997.*
Pritchard, J., et al.; Association Mapping in Structured Populations; May 2000; 12 pages.
Siepel, A., et al.; Combining Phylogenetic and Hidden Markov Models in Biosequence Analysis; Apr. 2003; 10 pages.
Siepel, A., et al.; Computational Identification of Evolutionarily Conserved Exons; Mar. 2004; 10 pages.
Hirschhorn, J., et al; Genome-Wide Association Studies for Common Diseases and Complex Traits; Feb. 2005; 14 pages.
Carrizo, S.; Phylogenetic Trees: An Information Visualisation Perspective; 2004; 6 pages.
Pollock, D, et al.; Coevolving Protein Residues: Maximum Likelihood Identification and Relationship to Structure; 1999; 12 pages.
Felsenstein. J.; Evolutionary Trees from DNA Sequences: A Maximum Likelihood Approach; 9 pages.
"An Overview of the CART Methodology", retrieved on Mar. 30, 2011 at <<http://www.researchmethods.org/CART_Overview.pdf>>, 4 pages.
Habib, et al., "Large Scale Genotype-Phenotype Correlation Analysis Based on Phylogenetic Trees", Bioinformatics, vol. 23, No. 7, 2007, pp. 785-788.
Treurnicht, et al., "Genotypic and Phenotypic Analysis of the Env Gene From South African HIV-1 Subtype B and C Isolates", Journal of Medical Virology, vol. 68, 2002, pp. 141-146.

* cited by examiner

*Primary Examiner* — Marjorie Moran
*Assistant Examiner* — Anna Skibinsky
(74) *Attorney, Agent, or Firm* — Lee & Hayes, PLLC

(57) ABSTRACT

Statistical models for identifying associations are described herein. By way of example, a system for identifying associations between variables can include a model builder and an association identifier. The model builder can receive observations about the variables and generate a null model and a non-null model. The association identifier can assess the strength of the association between the variables by determining how much the non-null model better explains the observed data than the null model. Additionally or alternatively, the structure of the observed data can be inferred simultaneously with the statistical model.

19 Claims, 14 Drawing Sheets

ROC on synthetic co-evolution data.

Calibration curve on synthetic co-evolution data.

ROC on synthetic conditional influence data.

Calibration Curve on synthetic conditional data

Estimated ROC on real HLA-amino acid associations.

Genotypic loci that are associated with bacterial resistance phenotypes avrRpm1 (top), avrRpt2 (middle) and avrPph3 (bottom). Vertical line indicates location of corresponding R gene.

IDENTIFYING ASSOCIATIONS USING GRAPHICAL MODELS

BACKGROUND

The search for correlations in many types of data, such as biological data, can be difficult if the data are not exchangeable or independent and identically distributed (IID). For example, a set of DNA or amino acid sequences are rarely exchangeable because they are derived from a phylogeny (e.g. an evolutionary tree). In other words, some sequences are very similar to each other but not to others due to their position in the evolutionary tree. This phylogenetic structure can confound the statistical identification of associations. For instance, although a number of candidate disease genes have been identified by genome wide association (GWA) studies, the inability to reproduce these results in other studies is likely due in part to confounding by phylogeny. Other areas in which phylogeny may confound the statistical identification of associations include the identification of coevolving residues in proteins given a multiple sequences alignment and the identification of Human Leukocyte Antigen (HLA) alleles that mediate escape mutations of the Human Immunodeficiency Virus (HIV).

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein facilitates the identification of associated or correlated variables using graphical models to remove and even leverage the non-exchangeability of data. By capturing this structure, these models yield well-calibrated false discovery rates and increase discriminatory power over standard methods that assume independence. The subject matter has many applications including but not limited to vaccine design for diseases such as Human Immunodeficiency Virus (HIV) infections, Acquired Immunodeficiency Syndrome (AIDS), Hepatitis C Virus (HCV) infections and malaria infections, as well as the development of treatments for diseases/conditions based on the results of genotype-phenotype association studies in biology and medicine and/or through the elucidation of protein structure.

By way of example, generative models that account for phylogenetic structure can be employed to improve the identification of associations. The phylogenetic structure of the data can be provided or learned simultaneously with the statistical models. To determine whether an association exists between target variable(s) and one or more predictor variables, two generative models can be created—a null model and a non-null model. The null model represents the null hypothesis that the data is accounted for by the phylogenetic tree alone and the non-null model represents the alternative hypothesis that the one or more predictor variables influence the target variable. Frequentist, Bayesian and cross-validation techniques then can be used to determine how much the non-null model better explains the observed data than the null model in order to assess the strength of association between the target variable and the one or more predictor variables. In the case of multiple target variables, the process described above can be repeated for each of the target variables. Optionally or alternatively, the predictor variables can be restricted for each of the multiple target variables in such a way that the resulting network of dependencies among predictor and target variables is a directed acyclic graph representing the relationships among the multiple variables.

The non-null models include a conditional model and a directed joint model. The conditional model is based on the assumption that the target variable evolves according to a phylogenetic tree having a topology and a branch length and is influenced by the one or more predictor variables at the tips of the tree. The directed joint model is based on the assumption that the target and one or more predictor variables coevolve, but that the influence between the variables is asymmetric (e.g., the predictor variable(s) influence the target variable, but not vice versa). Other evolutionary processes are possible and are within the scope of the subject matter described herein.

Although the examples described below are focused on the correlation of discrete (specifically binary) variables, the models can be generalized to multistate and continuous variables as well as to multiple predictor and target variables, thus producing a directed network (acyclic or otherwise) of relationships among multiple variables. The applications of multiple predictor variable models include but are not limited to learning the combined effects of drug and immune pressure on HIV evolution, identifying chains of compensatory mutations, learning the influence of diploid genes on phenotype and learning networks of interacting genes and proteins.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents.

DETAILED DESCRIPTION

Figure 1:
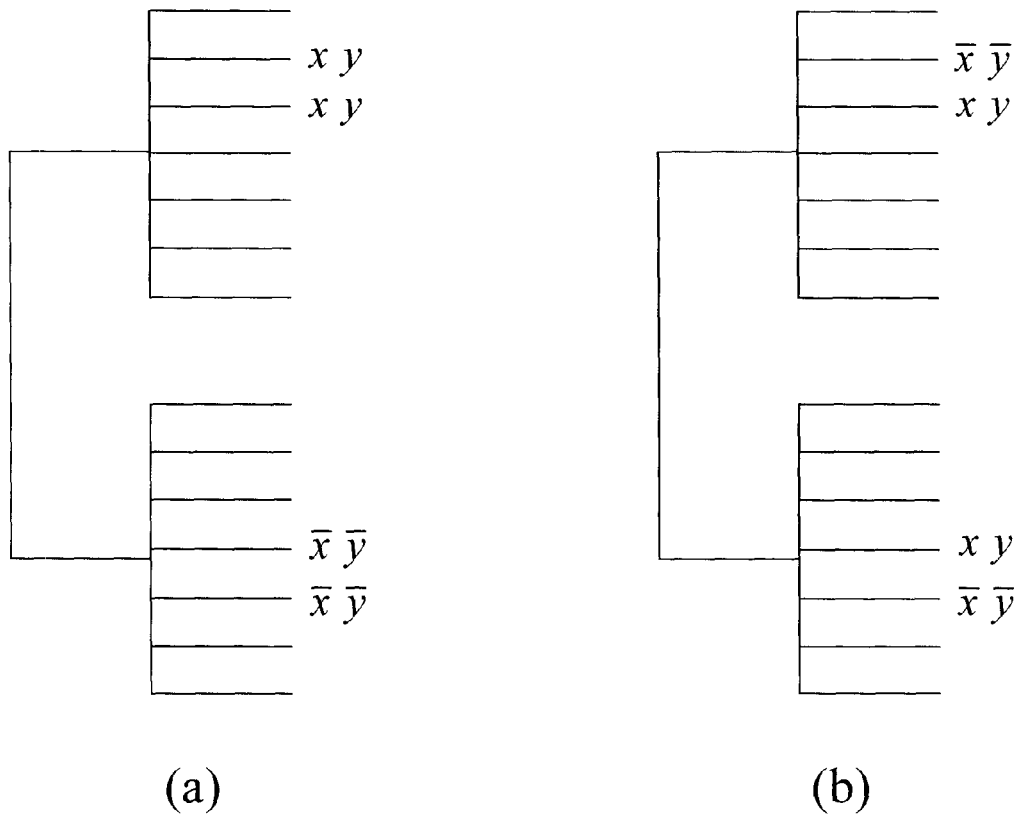
FIG. 1 schematically illustrates the (a) overcounting and (b) undercounting of evidence for an association between X and Y.

Simple statistical methods such as Fisher's exact test (FET) assume that data is infinitely exchangeable or identical and independently distributed (IID). However, biological data is not IID if it has a phylogenetic structure and this structure can easily confound the statistical search for associations within such data. The confounding effects of this structure have been revisited in multiple biological disciplines resulting in a disparate collection of proposed solutions. With few exceptions, these solutions fall short in one of two ways: (1) they seek only to calibrate p-values (e.g., Genomic Control); or (2) they assume a flat population structure (e.g., Structured Association, PCA). Statistical models known as generative or graphical models can be used to explicitly address both these issues. As shown in the Examples below, these models identify associations with fewer false positives and false negatives than existing methods. A method that accurately estimates the false positive rate of associations identified by the models is also described below.

Moreover, as shown below, no single corrective method or model is appropriate for all data sets. For instance, two evolutionary processes that incorporate phylogenetic structure are compared below—one process developed by others (Pollock et al.'s undirected joint model) assumes that two variables coevolve and the other process, a conditional process (conditional model), assumes that only one variable evolves according to a phylogenetic tree and makes no assumptions about how the second variable is distributed. Applying a distinct generative model for each of the two processes to real data indicates that the undirected joint model is better for some applications and the conditional model is better for other applications. The utility of these models in demonstrated three domains below: (1) HLA-mediated immune pressure on HIV evolution, (2) networks of compensatory mutations in an HIV protein, and (3) a genome wide association (GWA) study in which standard population structure-correcting methods are known to fail.

In order to understand the potential for confounding by phylogeny, it is helpful to examine the problem of identifying HLA-mediated immune pressure on HIV-1. Others have suggested that the immune pressure from the cellular arm of the immune system can exert substantial selection pressure on HIV. If a particular HLA allele exerts pressure on a certain amino acid in the HIV-1 genome, then a correlation between whether an HIV sequence has that amino acid and whether the patient infected with that sequence has the HLA allele should be detectable. One way in which to quantify the degree of association between these two observations is to count the number of patients with and without the allele and infected with strains of HIV with and without the amino acid and to apply a simple statistical test such as Fisher's exact test. This procedure, however, ignores the phylogenetic structure among the sequences.

Figure 2:
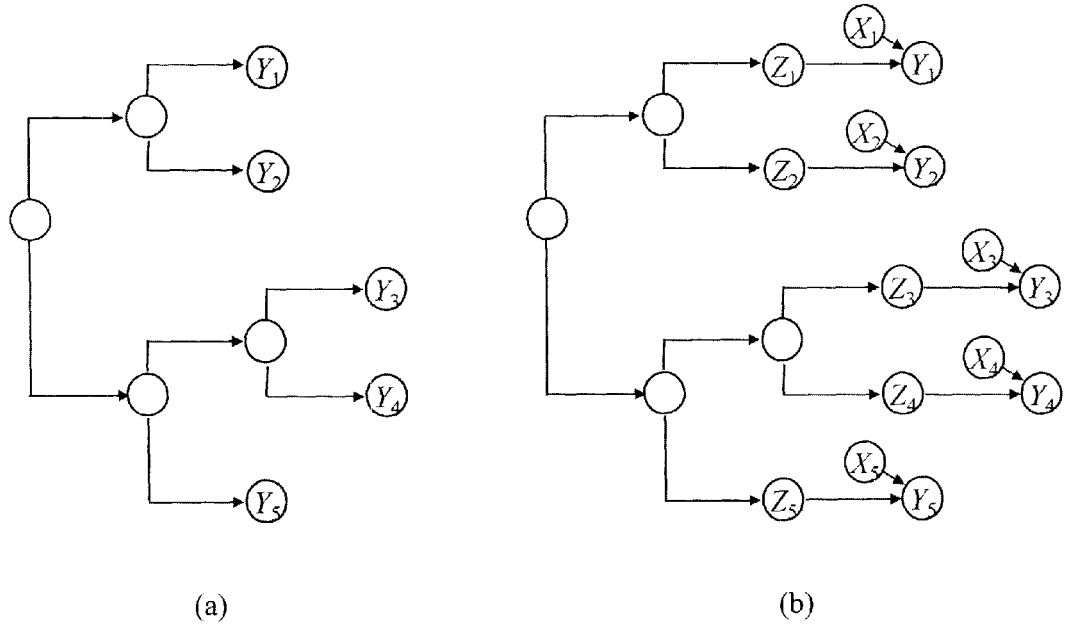
FIG. 2 schematically illustrates two generative (graphical) models (a) the single-variable model for Y and (b) the conditional model for Y given X. The variable $Z_i$ represents the variable $Y_i$ had there been no influence from $X_i$. Observed variables are shaded.

If, for instance, the HIV sequences have the phylogeny shown in FIG. 1(a), in essence, there are two clusters of sequences in which sequences within a cluster are similar to each other but quite different from those in the other cluster. If X and Y are present in the two sequences on the left and absent in the two sequences on the right, as shown in FIG. 1(b), the observations are well explained by the phylogeny alone and should not be treated as independent observations. Consequently, the application of Fisher's exact test or some other test that ignores the phylogenetic structure would overcount these observations when determining the correlation of X and Y. In contrast, if the observed data is as shown in FIG. 2(b), observing the presence and absence of the amino acid in the same branch of the phylogeny is quite surprising, unless the observations of Y are taken into account. In this example, the application of a statistical test that does not account for phylogeny would result in undercounting the associations when determining the correlation of X and Y.

The above example helps to illustrate a subtle distinction between two causal processes that can confound a search for correlations. In one process, X and Y coevolve according to the phylogenetic tree such that any change in Y during evolution influences the evolution of X, and vice versa. The phylogenetic tree serves as a confounder of X and Y in the traditional sense in that the tree is correlated with both X and Y. This leads to spurious correlations between X and Y when the tree is ignored. In the second process, only X evolves according to the tree. In contrast to the first process, the influence of Y on X occurs only at the tips of the tree. Y need not evolve according to the tree or "follow the tree," but instead can have any distribution, including one in which the observations of Y are IID. These two processes are referred to herein as coevolution and conditional influence, respectively. Confounding by phylogeny can happen in either case.

The subject matter described herein includes generative models that explicitly account for structured data to determine if two or more variables are correlated. The conditional model is based on the assumptions that only one variable (the target variable) follows a phylogenetic tree and that this target variable is influenced by one or more predictor variables at the tips of the tree. The directed joint model is based on the assumptions that all of the variables follow the same phylogenetic tree and that the predictor variable(s) influence the target variable at the tips of the tree but that the target variable does not influence the predictor variable(s). For both models, associations are identified by determining the degree to which these non-null models explain the data better than a null model that uses only the phylogeny to explain the data.

Both the conditional and directed joint models yield well-calibrated false discovery rates and increased discriminatory power over standard methods that assume independence. Studies using the models on both synthetic and real data were performed and the results showed that models that take phylogeny into account outperform models that do not (see Examples 1-4 below). As shown by the Examples below, the models have many practical uses, such as the identification of escape mutations in response to immune pressure, the prediction of coevolving peptide residues and genomic wide association (GWA) studies to identify genotype-phenotype correlations. In addition, the generative models can accurately distinguish between the processes of coevolution and conditional influence.

Overview of the Models

Generative models also are known as directed acyclic graphical (DAG) models. A generative model consists of (1) a directed acyclic graph in which nodes correspond to variables and arcs specify dependencies among the variables and (2) a set of conditional probability distributions, one distribution for each node, which describe how to generate an instance for that node given values for the parents of that node. A simple example of a generative model is a probabilistic phylogenetic tree. To generate data from such a model, the value of the root node is sampled from the (marginal) distribution associated with that node. Values for downstream nodes are then sampled, working from the root node to the tips. For any generative model, observations for some (and not necessarily all) nodes can be used to infer the distributions of the model. One commonly used criterion for inference is to identify the distributions that maximize the likelihood of the data.

Single-Variable Model

Before considering models of associations between variables, it is helpful to understand the situation in which a single binary variable Y, with possible states present (y) and absent ($\bar{y}$), is distributed according to a given phylogenentic tree. The acyclic graph of the generative model, which is simply the series of branches in the phylogenetic tree, is shown in FIG. 2(a). Nodes at the tips of tree, labeled $Y_1 \ldots Y_N$, correspond to the observations of Y. Unlabeled nodes in the interior of the tree correspond to events of divergence. (Although each $Y_1$ and interior node corresponds to a variable in the ordinary statistical sense, the collective of variables is sometimes referred to—Y in this case—as a variable. The proper meaning of the word should be clear from context.) To generate observations for $Y_1 \ldots Y_N$, a value for the root node is first sampled from the (marginal) distribution associated with that node. Values for downstream nodes are then sampled, working from the root node to the tips, using the conditional probability distribution at each node. As in the probabilistic model of Felsenstein J, "Evolutionary trees from DNA sequences: a maximum likelihood approach," *J Mol Evol* 1981, vol. 17(6), pp. 368-76, for a phylogenetic tree, the transition from state i to state j along a transition with branch length t is assumed to occur with probability $P_{ij}(t)$ that is determined by a continuous time Markov process (CTMP).

In the single binary variable case, the CTMP is parameterized by a rate parameter $\lambda$, which effectively scales the branch lengths, and the stationary probability $\pi=\Pr(Y=y)$, which is the probability of Y=y reached by the Markov process after an infinite amount of time. The instantaneous rate of change from $\bar{y}$ to y is $\lambda\pi$, yielding a transition probability matrix whose values as a function of time t are given by $$P_{ij}(t) = \begin{cases} \exp[-\lambda t] + \pi_i(1 - \exp[-\lambda t]) & \text{if } i = j \\ \pi_j * (1 - \exp[-\lambda t]) & \text{if } i \neq j. \end{cases} \quad (1)$$

Given a set of observations for Y at the tips of a tree, the parameters $\pi$ and $\lambda$ can be chosen to be those that maximize the likelihood of the data. Given these parameters, the phylogenetic tree $\Psi$, and the observed data $D_Y$, the likelihood $L(D_Y|\pi, \lambda, \Psi)$ can be computed. Any suitable method for identifying the maximum-likelihood parameters can be used, including but not limited to gradient decent, the Expectation-Maximization (EM) algorithm and coordinate descent, iteratively maximizing the likelihood for each parameter individually using Brent's method. This model is reversible, since $\pi_i P_{ij}(t) = \pi_j P_{ji}(t)$, which allows working with an unrooted (or arbitrarily rooted) tree. Also, this model includes the situation where the instances of Y are IID as a special case (i.e., when $\lambda$ is infinity).

Undirected joint model as described in Pollock et al., "Coevolving Protein Residues: Maximum Likelihood Identification and Relationship to Structure," *J Mol Biol*, vol. 287, pp. 187-198.

To determine whether a second binary variable X is correlated with Y, an association model developed by others, referred to as the undirected joint model, can be used. The undirected joint model is based on the assumption that X and Y coevolve according to the same phylogenetic tree and that, throughout the course of evolution, a change in either variable can influence the evolution of the other. This generative model can be thought of as a single-variable model for a variable XY representing the cross product of X and Y with the four states: xy, x$\bar{y}$, $\bar{x}$y, $\bar{x}\bar{y}$. The undirected joint model has five parameters: two rate parameters, $\lambda_X$ and $\lambda_Y$, and three parameters $\pi_{xy}$, $\pi_{x\bar{y}}$, $\pi_{\bar{x}y}$, and $\pi_{\bar{x}\bar{y}}$, representing the stationary distribution of XY. The instantaneous rate matrix Q is given by $$Q_{ij} = \begin{pmatrix} xy \\ x\bar{y} \\ \bar{x}y \\ \bar{x}\bar{y} \end{pmatrix} \begin{pmatrix} -\sum & \lambda_Y \pi_{xy}/\pi_x & \lambda_X \pi_{xy}/\pi_y & 0 \\ \lambda_Y \pi_{xy}/\pi_x & -\sum & 0 & \lambda_X \pi_{xy}/\pi_y \\ \lambda_X \pi_{xy}/\pi_y & 0 & -\sum & \lambda_Y \pi_{xy}/\pi_x \\ 0 & \lambda_X \pi_{xy}/\pi_y & \lambda_Y \pi_{xy}/\pi_x & -\sum \end{pmatrix}, \quad (2)$$

where the diagonal entries assure that the rows sum to 0. Given a particular branch with length t, the probability that one instance of XY transitions to another can be computed by determining P=exp[Qt] using standard numerical Eigen-decomposition techniques. The undirected joint model treats X and Y symmetrically so that the influence of X on Y and Y on X is "undirected" (hence the name for the model).

Directed Joint Model

Pollock et al.'s undirected joint model assumes a symmetric or undirected relationship between two coevolving variables X and Y. In contrast, the directed joint model assumes coevolution like the undirected joint model, but assumes that the relationship between the two or more variables is asymmetric or directed in that one or more variables (predictor variables) influence one or more target variables but not vice versa. In this evolutionary process, the one or more predictor variables evolve as in the single-variable model but the target variables evolve with a rate that depends on whether the one or more predictor variables are absent or present. The transition probability matrix for the model is given by the following:

$$Q_{ij} = \begin{pmatrix} xy \\ x\bar{y} \\ \bar{x}y \\ \bar{x}\bar{y} \end{pmatrix} \begin{pmatrix} -\sum & \lambda_{Y|x} \pi_y & \lambda_X \pi_{\bar{x}} & 0 \\ \lambda_{Y|x} \pi_y & -\sum & 0 & \lambda_X \pi_x \\ \lambda_X \pi_x & 0 & -\sum & \lambda_{Y|\bar{x}} \pi_y \\ 0 & \lambda_X \pi_x & \lambda_{Y|\bar{x}} \pi_y & -\sum \end{pmatrix}, \quad (3)$$

where the diagonal entries assure that the rows sum to 0. This model, like the undirected joint model has five parameters: $\pi_x$, $\pi_y$, $\lambda_X$, $\lambda_{Y|x}$, and $\lambda_{Y|\bar{x}}$. As in the undirected case, the probability that one instance of XY transitions to another along a branch of length t is computed by determining P=exp[Qt] using standard numerical Eigen-decomposition techniques.

To determine the significance or strength of the correlation between X and Y, a measure of how much better this model explains the data than a null model in which each variable independently follows the single-variable model is generated. Any suitable method can be used to determine the non-null model's ability to better explain the data including but not limited to frequentist methods, Bayesian methods and cross validation. By way of example, in the frequentist case, a p-value using a likelihood ratio test can be computed, which is justified since the null model is nested within the alternative model. Multiple tests can be controlled for by using q-values, which are estimates of false positive rate. In the Bayesian case, a Bayesian information criterion (BIC) can be used to select the non-null model over the null. Cross-validation techniques also can be used. This technique entails partitioning the data is into K sets of roughly equal size and for each partition, all remaining partitions are used to learn the parameters of a model which is then used to predict the data in the distinguished partition. The non-null model is deemed better than the null model if the predictions of the non-null model (over all partitions) are better than those of the null model. Numerous scoring rules, which assign a number to a given prediction, are possible such as the log scoring rule: log p(data|model).

Conditional Model

For certain types of observed data, it is reasonable to assume that Y (referred to as the target variable) follows a phylogenetic tree and that the influence of X (referred to as the predictor variable) on Y occurs only at the tips of the tree, but it is not reasonable to assume that X follows the same tree (or any tree at all). This situation can arise if, for example, Y represents the amino acid at a particular position in a sequence and X represents an environmental variable suspected of being a source of selective pressure on X (e.g., HLA alleles that exert pressure on specific pathogens, such as HIV, to select for escape mutations). Whereas the amino acid likely follows the phylogenetic tree of its protein, it is unreasonable to expect that the HLA types follow that same tree (except perhaps at the lade level, where HLAs may be distributed similarly to the clades of the HIV species tree due to similar geographic constraints). Furthermore, although it is reasonable to assume that HLA pressure acts continually throughout evolution, this pressure is distributed randomly along the evolutionary paths, and consequently the influence of the known HLA of a patient will only appear at a tip of the tree.

The conditional model captures these notions. The conditional model is a single-variable model for the target variable Y modified to include the influence of X at the tips of the tree. To construct the conditional model, we start with the single-variable model for Y as illustrated in FIG. 2(a) and change each $Y_i$ to $Z_i$, which represents what $Y_t$ would have been had there been no influence from $X_t$. We then make each $Y_i$ a probabilistic function of $X_t$ and $Z_t$, encoding this function with a probability matrix. There are four possible single-parameter transition matrices. Using names inspired by the influence of HLA mediated immune pressure on HIV mutation, the four cases are as follows:

1) Escape X=x increases the probability of y→$\bar{y}$ transitions,
2) Attraction X=x increases the probability of $\bar{y}$→y transitions,
3) Reversion X=$\bar{x}$ increases the probability of $\bar{y}$→y transitions,
4) Repulsion X=$\bar{x}$ increases the probability of y→$\bar{y}$ transitions.

As in the directed joint case, frequentist methods (likelihood ratio test), Bayesian (BIC) methods and cross validation can be used to determine the degree to which this model better explains the data for Y than does the single-variable (null) model for Y. The explanation of the data for X need not be considered, as the model is a conditional one. The conditional model is reversible in the sense that the choice of root node among non-tip nodes does not affect the likelihood of the data.

Although it is possible that, for example, both escape and reversion processes are acting at the same time, allowing for two or more processes at the same time dramatically reduces the power of the model. Consequently, for any given pair of variables, one model can be chosen from the set above that best explains the data for those variables. Frequentist and Bayesian methods as well as cross validation can be used to make this choice. In the frequentist case, the model with the lowest q-value can be chosen and in the Bayesian case, the model with the largest BIC score can be chosen.

The conditional model can be used to identify associations between both discrete and continuous variables. In the case in which the target variable is a discrete variable and the one or more predictor variables are discrete or continuous, the target variable can be modeled as a logistic regression of the predictor variables. In the case in which the target variable is a continuous variable and the one or more predictor variables are discrete or continuous, the target variable can be modeled as a linear regression of the predictor variables.

Learning the Phylogenetic Tree Simultaneously with the Statistical Model

The phylogenetic tree can be learned simultaneously with the statistical models, for instance, by using an iterative, hill-climbing algorithm. Such an algorithm can include the following steps, for instance:

1) learn a phylogenetic tree assuming no associations in any suitable method, such as by using the standard techniques published in the literature;
2) identify associations using for instance, the models described above and either a Bayesian or frequentist cutoff for relevance;
3) assume these associations are true, relearn the structure and parameters of the phylogenetic tree using standard techniques except that the likelihood of the data changes due to the presence of associations in the generative model of the data; and
4) repeat steps 2 and 3 until the associations identified are fairly stable.

Methods

The models were compared using both synthetic and real data sets. Using synthetic data, two questions were examined:

1) does taking phylogeny into account indeed improve the analysis (i.e., when data is generated under the undirected joint or conditional models, do these models perform better than Fisher's exact test (which assumes the data to be IID)); and
2) when data is generated under the undirected joint model, does that model better fit the data than the conditional model, and vice-versa?

Two criteria were used to measure the performance of a model. First, the ability of the model to discriminate true from false correlations was measured via Receiver Operator Characteristic (ROC) curves, which are plots of true positive versus false positive rates. A q-value for every pair X-Y that was tested was computed and every test with a q-value less than some threshold $q_0$ was deemed to be a real association. The known true and false associations in the synthetic data were then used to compute true positive and false positive rates for that threshold. The threshold $q_0$ was varied, producing the ROC curve. Second, the calibration (the degree to which the q-value is a good estimate of true false positive rate of the model) was measured. ROC performance is independent of calibration, as any monotonic transformation of the threshold used to compute an ROC curve (q-values in this case) leaves the curve unchanged.

Using real data, the question examined was whether the undirected joint model or conditional model better represent the data. Because it is unknown whether a discovered association is real or not, the ROC or calibration criterion described above were not used to evaluate performance. Furthermore, because neither model is nested within the other, Bayesian methods were chosen for the comparison, in particular, the Bayesian information criterion (BIC). The BIC score for a model with maximum-likelihood parameter $\theta$ and d free parameters is given by $\log p(\text{data}|\text{theta}, \text{model}) - d/2 \log N$. The BIC is an asymptotic approximation to the marginal likelihood of a model—a Bayesian measure of how well the model represents the data.

To compare the conditional model (a model for Y given X) to the undirected joint model (a model for X and Y), the sum of the overall BIC scores for the conditional model and the single-variable model for X was compared to the overall BIC score for the joint model. The overall BIC score for the conditional model is the highest BIC score among the conditional models (escape, attraction, reversion, and repulsion) and the independence (null) model. The overall BIC score for the undirected joint model is the higher of the BIC scores for the undirected joint model and the independence model. To test whether there is a significant difference between the overall scores for the conditional and undirected joint models, a two-sided, paired Wilcoxon test was applied to these scores across all X-Y pairs in the data.

It sometimes can be useful to test whether a variable follows a given phylogenetic tree. To do so, the difference in BIC scores for the ordinary single-variable model for that tree and a model that assumes the variable is IID (a single-variable with $\lambda \rightarrow$ infinity) can be calculated. The variable follows the tree if the difference in scores is greater than zero.

HIV aligned sequences and HLA data from the Western Australia cohort (HIV sequence accession numbers AY856956-AY857186) were obtained. Some anomalies were noted in the p6 section and these were corrected by hand. The phylogenetic trees for Examples 2 and 3 below were constructed from the full Gag DNA alignment by applying PHYML with the general reversible model, optimized tree topology, maximum likelihood estimates for the base frequencies, estimated proportion of invariable sites, and four substitution rate categories with an estimated gamma distribution parameter. When identifying associations, amino acids were binarized such that a single association test compared the presence or absence of the residue in question. Ambiguity codons were treated as uncertainties. For example, if a codon was X or Y, then it was treated as unknown for codon X, but known to be false for codon Z.

The *Arabidopsis* data set was taken from Aranzana et al., "Genome-Wide Association Mapping in *Arabidopsis* Identifies Previously Known Flowering Time and Pathogen Resistance Genes," PLoS Genet., 1(5):e60. November 2005. The phylogeny was built from a set of sequences consisting of positions in the locus alignments for which at least two sequences differed from the consensus. For each genotyped locus, haplotypes were identified according to sequence identity after removing positions for which only one sequence varied from the consensus. All sequences that accounted for less than 5% of the data were clustered together.

The independence (single variable or null) models are nested inside the undirected joint and conditional models and contain one less parameter. Therefore, the asymptotic distribution of the log-likelihood ratio is $\chi^2$-distributed with one degree of freedom from which p-values can be computed. Simple p-values are, however, of limited use in the context of high levels of multiple hypothesis testing. Whereas a Bonferroni correction could be used to limit false positives, the high number of tests (typically in the tens or hundreds of thousands) forces an almost complete loss of power. Consequently, q-values were used to control for multiple tests.

To compute a q-value, first a false discovery rate (FDR) was computed, which measures the expected number of fraction of positives for any given p-value threshold $p_0$. For a given $p_0$, the estimate of FDR is the ratio of the expected number of associations with $p < p_0$ under the null distribution to the observed number of associations with $p < p_0$ in the real data. In the experiments, ten associations were generated under the null model for each examined X-Y pair to compute the expectation under the null. (The true FDR can be computed using null data that is generated only from observed values from which clearly non-null data have been removed. As only a small number of associations that were tested are real, the inclusion of null data generated from these associations introduces a small, conservative bias in the estimate of FDR). The q-value was computed to be the minimum FDR seen for $p_i \geq p_0$. This guarantees that q is a monotonic increasing function of $p_0$. (In general, FDR is expected to be a monotonic function of $p_0$, but is rarely monotonic in practice due to, e.g., variance in the statistic.)

When testing for an association between variables X and Y, null data can be generated in one of four ways: permute the instances of X, permute the instances of Y, parametrically bootstrap the instances of X, or parametrically bootstrap the instances of Y. The best method (e.g., the one that most accurately constructs the null data) depends on the data set being analyzed. For example, if data in which both the predictor and target variable follow a given phylogenetic tree is being analyzed, parametrically bootstrap either the target or predictor variable can be chosen because doing otherwise would produce data that no longer follows the tree and this would introduce a bias in the null data. In contrast, if data in which the predictor variable is IID and the target variable is not well described by the tree is being analyzed, permuting the instances of the predictor variable can be chosen because (1) the variable remains IID under permutation and (2) a parametric bootstrap of the target variable under the assumption that the data follows the tree would produce biased data. The best method for generating null data may also depend on the model being used to analyze that data as the undirected joint and conditional models can be sensitive to different biases in the data.

A systematic approach for determining which null-generation method to use for a given data set and given model was developed for analyses based on two observations. First, as the computation of q-values depends on the distribution of p-values under the null hypothesis, it is useful to select a null-generation method that produces an accurate distribution of p-values. Second, in all the data sets that were analyzed, the vast majority of variable pairs were not associated (i.e., they satisfied the null distribution). Consequently, given a data set and a given model for analysis, the data-generation method was chosen by identifying the one that yielded a distribution of p-values that most closely matched that produced by the given (real) data.

This approach resulted in the following choices being made: permutation bootstrap of the predictor variable for Examples 2 and 4 below, and parametric bootstrap of the predictor variable for Example 3 below. For the analysis of synthetic data (Example 1 below), null-generation methods that would preserve the known distributions of the predictor and target variables wee used: permutation bootstrap of the predictor variable for the conditional influence data set and parametric bootstrap of the predictor variable for the coevolution data set.

When computing q-values, it is sometimes useful to partition the tests into two or more sets to obtain more informative values. For example, a set of tests can be partitioned into two sets A and B corresponding to positive and negative correlations, respectively and for simplicity, assume the null distributions underlying A and B are identical. If A and B have the same number of associations with $p<p_0$, then $q_A(p_0)=q_B(p_0)=q_{A \cup B}(p_0)$. If A has a higher number of associations with $p<p_0$ than does B however, then $q_A(p_0)<q_{A \cup B}(p_0)<q_B(p_0)$. Computing q-values with respect to the merged set of associations will inflate the q-values of the associations in A and deflate the q values of the associations in B. Whereas q is still the expected number of false positives, computing $q_{A \cup B}(p_0)$ assures that the majority of those false positives are in B and some true positives in A are likely to be lost. The disadvantage of partitioning the tests is that more null data must be generated in order to preserve the variance of the estimate for q.

Tests can be split along natural boundaries. In the experiments using the conditional model, q-values were computed separately for each possible transition matrix (escape, attraction, reversion, and repulsion). For the undirected joint model and when computing Fischer's exact test (FET), q-values were computed separately for positive and negative correlations.

Synthetic data was generated to approximate real data as closely as possible. In the case of synthetic conditional influence, the conditional model was first applied to the real HLA data set to obtain reasonable parameter values. To generate predictor variables, the real HLAs were permuted to ensure IID distributions. For each association in the real data set, synthetic target data was generated in one of two ways: (1) if the association was significant (q<0.30), the corresponding synthetic HLA and the parameters learned on the real HLA-amino acid pair and generated data for the target variable were taken; otherwise (2) the target variable data was generated using the parameters learned by the single variable model. Because there were only twenty six significant associations, five synthetic associations were generated for each real association. For each replicate, a different synthetic HLA was chosen using the five HLAs whose frequencies most closely matched that of the real HLA on which the association was based.

In the case of coevolution, the undirected joint model was first fit to the HIV p6 data set, and then synthetic associations were generated using the learned parameters. For these data, one synthetic association was generated for each real association (q<0.30). For all non-significant real associations, the predictor and target variables were generated using the single-variable model with the parameters learned by that model on the real data.

Example 1

Experiments with Synthetic Data

Two synthetic data sets were constructed—one generated by the process of conditional influence (e.g., by a conditional model) and the other generated by coevolution (e.g., by the undirected joint model). The data sets representing conditional influence and coevolution were patterned after the real data sets of Example 2 (effects of immune pressure on HIV mutation) and Example 3 (pairwise amino-acid correlations) below, respectively. In particular, the sample size (N) and number of tests in the data sets were those of the corresponding Examples. In addition, the parameters of the generating model for conditional influence (coevolution) were taken from those of a conditional (undirected joint) model fit to the real data. The predictor (HLA) observations for the data set reflecting conditional influence were generated from an IID model.

Figure 3:
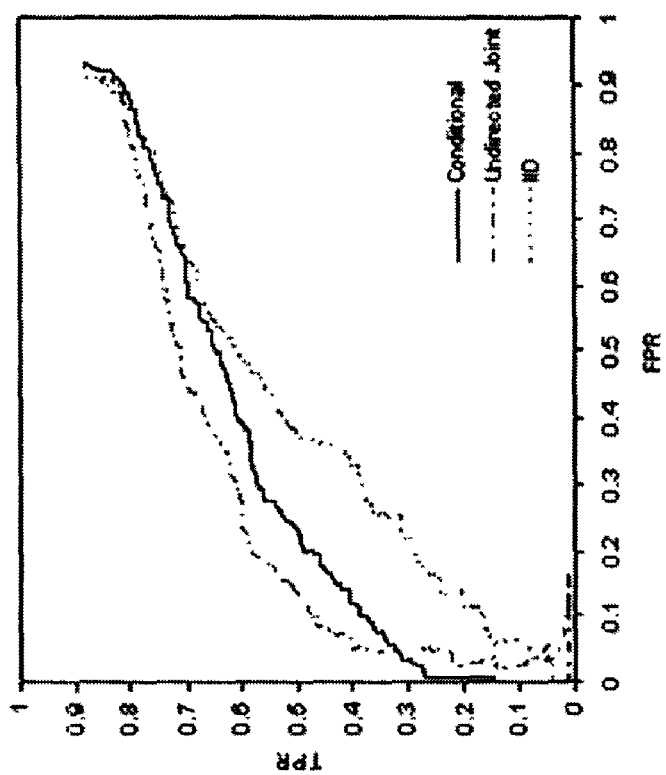
FIG. 3 shows Receiver Operating Characteristic (ROC) curves for synthetic coevolution data.
Figure 4:
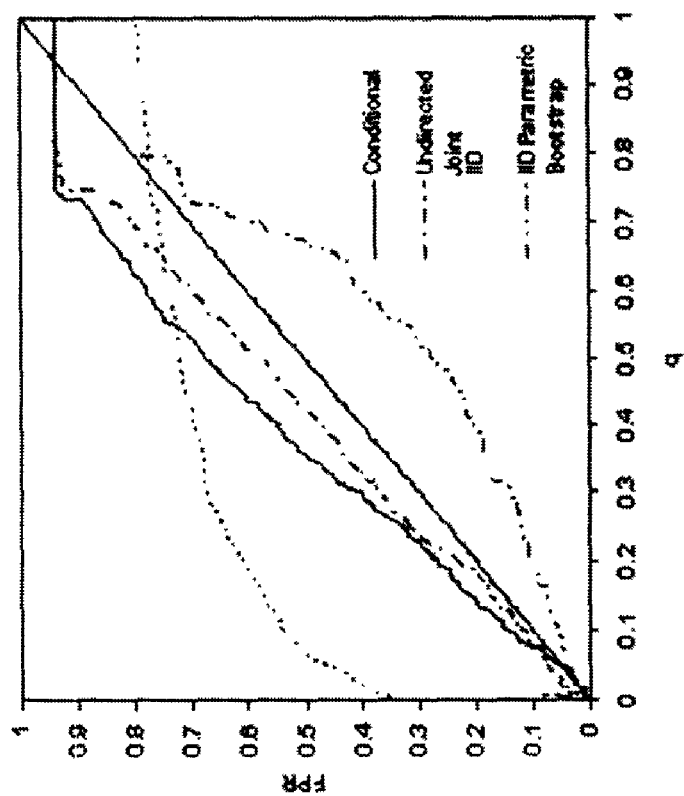
FIG. 4 shows the calibration of q-values on synthetic coevolution data.
Figure 5:
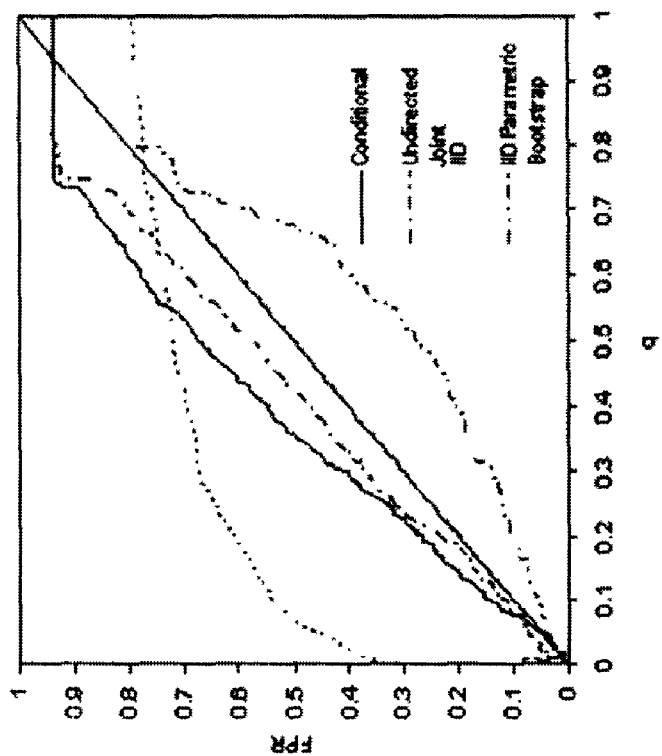
FIG. 5 shows ROC curves for artificial conditional influence data.
Figure 6:
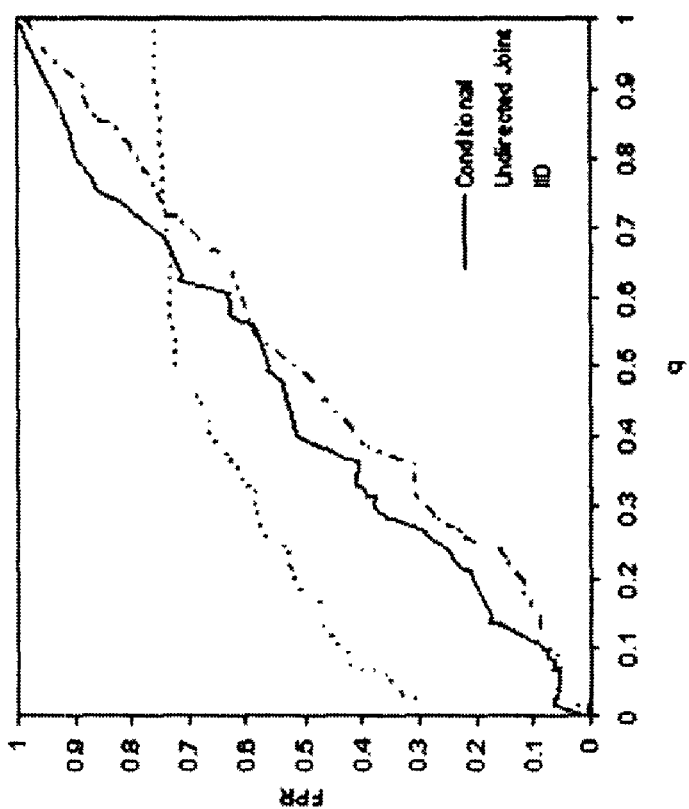
FIG. 6 shows the calibration of q-values on synthetic conditional influence data.

As expected, when the data were generated according to the undirected joint model, the undirected joint model was the most discriminating, followed by the conditional and IID models (FIG. 3). The q-value calibration of the undirected joint model was slightly better than the conditional model, while the IID model was poorly calibrated (FIG. 4). Conversely, when the data were generated according to the conditional model, the conditional model was the most discriminating, followed by the IID and undirected joint models (FIG. 5). Both the conditional and undirected joint models were well calibrated, whereas the q-values of the IID model (FET) tended to overestimate the false positive rate (FIG. 6). Thus, not only does taking phylogenetic structure into account improve the analysis, but the two models can distinguish between the processes of coevolution and conditional influence.

In both examples, the q-values from FET underestimated the false positives rates (i.e., were liberal). Although liberal estimates are to be expected when the data is generated by coevolution because the tree is a hidden common cause of X and Y, the conditional model may produce liberal or conservative estimates of false positive rates depending on whether data is over or undercounted as described above. On other data sets, FET produces both liberal and conservative estimates of false positive rate.

To validate the use of the BIC to evaluate model performance on real data, the BIC scores of the undirected joint and conditional models on the synthetic data sets were compared representing conditional influence and coevolution. As expected, the conditional model had a significantly higher likelihood than the undirected joint model on the conditional-influence data set ($p=7.6 \times 10^{-53}$, N=157317), and the joint model performed better model on the synthetic coevolution data set (p=0.06, N=10025). Moreover, over a wide variety of data sets, the conditional model runs an order of magnitude faster than the undirected joint model, which requires optimization over a larger number of parameters and more complex Eigen decompositions.

Example 2

Effect of Immune Pressure on HIV Evolution

To investigate the effects of immune pressure on HIV evolution, Moore et al. (see "Evidence of HIV-1 adaptation to HLA-restricted immune responses at a population level," *Science*, 296: 1439-1443. May 2002) obtained HIV sequences from 234 individuals along with the HLA-A and HLA-B alleles of the infected individuals. Performing several analyses (all of which assumed the data to be IID), they found strong correlations between the presence or absence of amino acids at particular positions and the presence or absence of particular HLA alleles in the infected patients, presumably reflecting the "escape" of amino acids under immune pressure.

The MHC-I alleles (N=205) from the Moore et al. data set were reanalyzed using both the conditional and undirected joint models. First, a phylogenetic tree was constructed from the full set of sequences (see Methods above). The single-variable model then was used to determine whether any HLA alleles followed the tree. Two pairs of HLA-1 alleles—B*4201, C*1701, and A*0207, B*4601 (where each pair is in tight linkage disequilibrium)—were found to follow the tree. Thus, the HLA data was separated into two sets: (1) "C1701" consisting of these four alleles and (2) "notC1701" consisting of the remaining alleles, and these two sets were analyzed separately.

The results using BIC showed that the conditional model better explains the notC1701 data (p=0.0001, N=256296), whereas the undirected joint model better explains the C1701 data (p=1.9×10$^{-24}$, N=5664). In the case of the C1701 data, it seems that the phylogenetic tree is a confounder of the data in the traditional sense (i.e., the tree is associated with both the HLA and the sequences and induces false correlations between HLA and sequence). In the case of the notC1701 data, the tree does not induce false associations. Rather, phylogenetic correction apparently improves over an IID analysis by avoiding the over and/or undercounting of data as described above.

Figure 7:
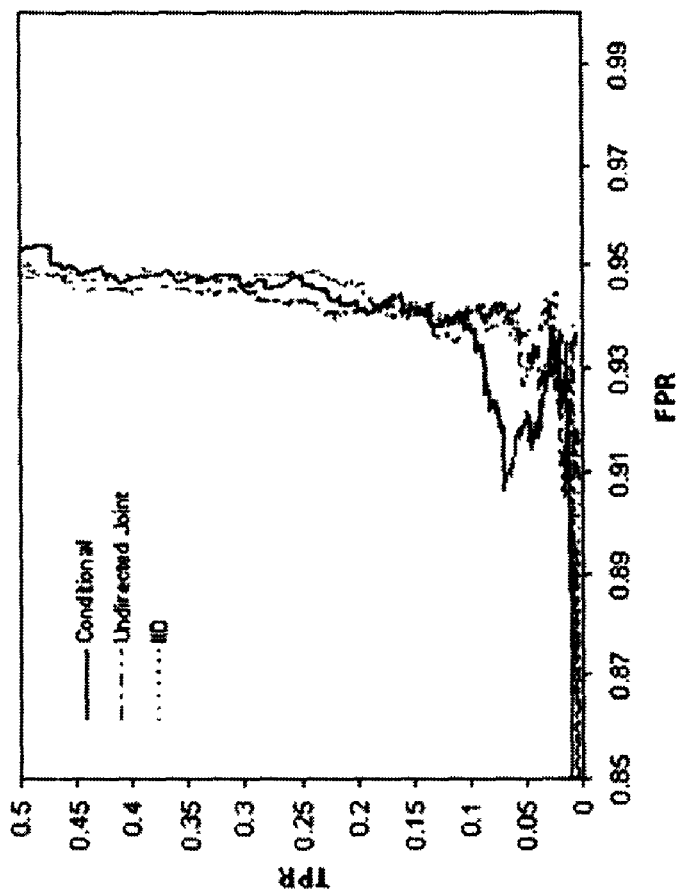
FIG. 7 shows ROC curves for the real full HLA-amino-acid data. Ground truth was estimated by identifying known epitopes within three residues of the predicted association.

Additional information was used to help confirm the HLA-sequence associations that were identified. In particular, since immune pressure is focused on epitopes and the immediate surrounding regions that participate in the presentation of those epitopes on the HLA molecules at the cell surface, a known epitope in the vicinity of an identified association supports the validity of that association. Accordingly, ROC curves were constructed in which an HLA-sequence association was considered "true" if it was within three amino acids of a known epitope for the corresponding HLA and "false" otherwise. Although this method does not take into account undiscovered epitopes or linkage disequilibrium, it should nonetheless be unbiased with respect to a comparison of the alternative methods for identifying associations. The ROC curve in FIG. 7 for the notC1701 data is consistent with the BIC and synthetic results, indicating that the conditional model best fits this data. An ROC curve for the C1701 data could not be constructed because there are no known A*0207, B*4201, B*4601 or C*1701 epitopes in Gag. The associations found applying the conditional model with q<0.2 to the real data are shown in Table 1 below.

TABLE 1

Predicted HLA-amino acid associations in Gag.

| Position | HLA allele | p-value | q-value |
|---|---|---|---|
| 242 | B5701 | 4.3E−08 | 0 |
| 28 | A0301 | 1.5E−07 | 0 |
| 242 | B5801 | 3.2E−06 | 0.03 |
| 147 | C0602 | 5.0E−06 | 0.03 |
| 26 | C0303 | 6.9E−06 | 0.05 |
| 482 | B4001 | 2.8E−05 | 0.1 |
| 397 | A3101 | 3.8E−05 | 0.13 |
| 495 | B4701 | 6.9E−05 | 0.17 |

Example 3

Pairwise Correlations Between Amino Acids in HIV

Identification of pairwise correlations between amino acids is important for many biological applications because correlations can indicate structural or functional interaction (e.g. identifying correlated protein residues to predict secondary/tertiary/quaternary protein structure). Both the undirected joint and conditional models were applied to the sequence data from the Western Australia cohort. A fifty-two amino acid HIV-1 p6 protein (which is cleaved from the Gag[55] polyprotein) was chosen because it is the shortest HIV protein, which facilitated making pair-wise amino acid tests feasible for all models. The conditional model was fit in both directions (making both X and Y target variables) and the best model was selected according to BIC.

The BIC scores of the conditional model were significantly higher than those of the undirected joint model (p<10$^{-100}$, N=52767). One possible explanation for why the conditional model proved better may be because many mutations could be compensating for other mutations driven by HLA immune pressure. The conditional model determined that 893 of the 52767 (1.7%) amino acid pairs and 310 of 1300 (24%) of position pairs are correlated at q<0.2. This dense network of interaction is consistent with the idea that many of the mutations are compensatory in nature. For example, the conditional model identified two HLA-mediated escape mutations in p6 (see Table 1 above). Mutations at these two positions accounts for 42 (13.5%) of the position-pair correlations.

Example 4

Genomic Search for Genotype-Phenotype Associations in Arabidopsis thaliana

Aranzana et al. recently demonstrated the potential utility of genome wide association (GWA) studies, as well as the importance of accounting for phylogenetic structure. In this study, the authors genotyped 848 loci in 96 Arabidopsis thaliana strains and looked for haplotypes that were correlated with hypersensitive response to P. syringae strains expressing one of three avirulence (avr) genes (avrRpm1, avrRpt2 or avrPph3). In plants, each avr bacterial protein is recognized by a corresponding resistance (R) gene. If both plant and pathogen have active copies of the respective avr-R genes, a biochemical cascade is triggered at the point of infection, leading to massive programmed cell death and containment of the infection. Using both an IID-based model and a method that used the phylogenetic structure that was constructed from the sequenced loci, the authors showed that loci adjacent to the known R genes are highly correlated with the corresponding avr phenotypes. The authors noted that their statistics were poorly calibrated, precluding confident predictions of the other pathogen-response proteins that are involved in the hypersensitive response cascade.

The well-calibrated conditional model was applied to the same data using a phylogenetic tree constructed from the sequence data. When applying the conditional model to this data, it was not initially clear whether the target variables should be haplotypes or phenotypes. In general, genetic variations directly influence phenotypes, but phenotypes also indirectly influence haplotypes through selection pressure. Furthermore, the analysis indicated both haplotypes and phenotypes largely followed the phylogenetic tree (61% of the haplotype alleles and two of the three avr phenotypes). Consequently, the conditional model was run in both directions (using the phenotypes as the target and again using the phenotypes as the predictor) using BIC to determine which direction was best for any given haplotype-phenotype pair.

Figure 8:
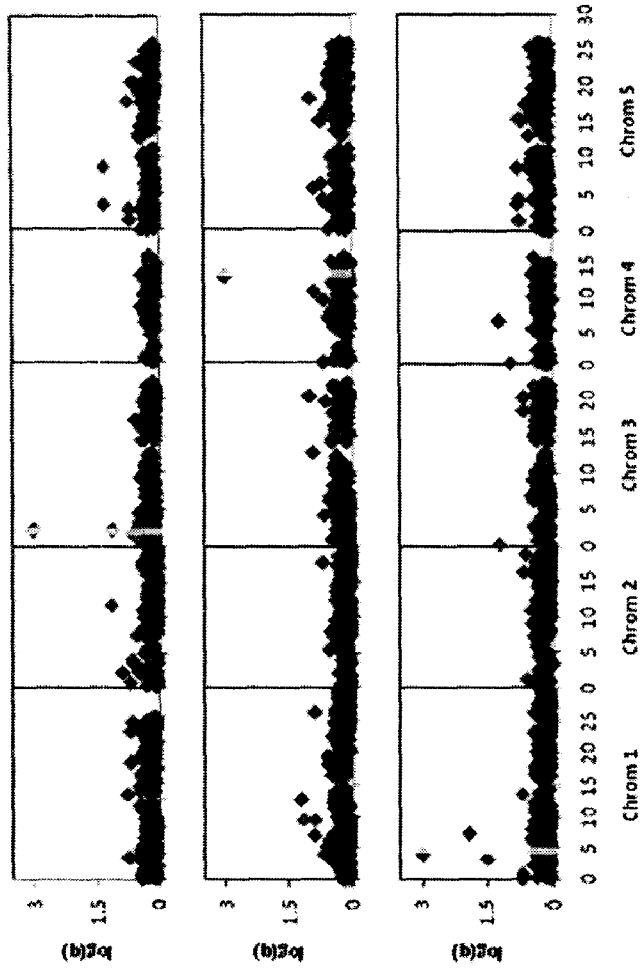
FIG. 8 shows the genomic distribution of genotype-phenotype association scores for *Arabidopsis* bacterial response. 4681 haplotypes were compared against each of the three bacterial response phenotypes, Rpm1 (Top), Rpt2 (Middle) and Pph3 (Bottom). For each haplotype, the four conditional models were run and negative $\log_{10}$ of the most significant q value were plotted. For each phenotype, the most significant association was a locus within 10 Kb of the corresponding R gene. The dotted line shows the q=0.20 threshold. 74% of the loci with q<0.2 ($\log_{10}(q)$>0.7) are near known or putative bacterial response loci.

The BIC scores for the conditional and undirected joint models were not significantly different (p=0.70, N=14043) and the results of the conditional model were examined in detail. FIG. 8 shows the genome wide distribution of conditional influence q-values for each of the three phenotypes. For each phenotype, the most significant association is a locus near the corresponding R gene.

If the methods are indeed calibrated, then roughly 80% of the associations identified using a q<0.2 cutoff should be legitimate. To explore this conjecture, fifty-one genotypic associations (comprising forty unique loci) that correlated with these three hypersensitive phenotypes at this cutoff (see Table 2 below) were examined to determine which of the associated loci were near known or putative bacterial response proteins thought to participate in the hypersensitive response cascade (data obtained from http://www.arabidopsis.org). Thirty six (71%) of the predictions were within 250 kilobases (Kb) and forty-four (86%) were within 500 Kb of such response proteins.

TABLE 2

Genotype-Phenotype Associations for *Arabidopsis thaliana*

| avr | Chrom | Locus | qValue | Annotation |
|---|---|---|---|---|
| avrPph3 | 1 | 3,294,414 | 0.158333 | 150 Kb from AT1G09665 pDRP |
| avrPph3 | 1 | 4,142,402 | 0 | 3 Kb from RPS5 known R. Inside RFL1 (At1G12210), which has high sequence similarity to RPS5 |
| avrPph3 | 1 | 7,341,614 | 0.073333 | 800 Km from AT1G22900, contains disease resistance response protein |
| avrPph3 | 2 | 11,456,847 | 0.073333 | 30 Kb from AT2G26910 ABC transport protein ⇓.200 Kb from AT2G26380 DRP-related. |
| avrPph3 | 3 | 70,672 | 0.073333 | ? |
| avrPph3 | 3 | 20,327,825 | 0.028571 | 100 Kb from AT3G55110 and AT3G55100 ABC trasporters ⇑.150 Kb from AT3G55230 pDRP |
| avrPph3 | 5 | 8,331,140 | 0.1 | 400 Kb from AT5G23400 pDRP |
| avrPph3 | 5 | 10,102,075 | 0.073333 | 600 Kb from AT5G27060 pDRP |
| avrRpm1 | 1 | 3,398,022 | 0.116667 | 250 Kb from AT1G10920 pDRP |
| avrRpm1 | 1 | 9,973,016 | 0.134783 | 500 Kb from AT1G27180 |
| avrRpm1 | 1 | 15,633,694 | 0.082353 | ? |
| avrRpm1 | 1 | 19,505,630 | 0.166667 | 200 Kb from AT1G52900 pDRP⇑ |
| avrRpm1 | 2 | 2,037,121 | 0.138889 | ? |
| avrRpm1 | 2 | 7,352,222 | 0.073333 | 40 Kb from AT2G16870 pDRP |
| avrRpm1 | 3 | 2,214,965 | 0 | 10 Kb from RPM1 (AT3G07040) known R. |
| avrRpm1 | 3 | 2,216,613 | 0 | 10 Kb from RPM1 (AT3G07040) known R. |
| avrRpm1 | 3 | 2,231,413 | 0 | 10 Kb from RPM1 (AT3G07040) known R. |
| avrRpm1 | 3 | 3,176,691 | 0.133333 | 1 Mb from RPM1. |
| avrRpm1 | 4 | 1,242,552 | 0.155 | 300 Kb from AT4G02170 pDRP |
| avrRpm1 | 4 | 6,131,588 | 0.1375 | 150 Kb from AT4G09430 pDRP |
| avrRpm1 | 5 | 1,362,872 | 0.066667 | Inside AT5G04720 pDRP |
| avrRpm1 | 5 | 3,392,409 | 0.044444 | 200 Kb from AT5G11250 pDRP. |
| avrRpm1 | 5 | 9,925,437 | 0.073333 | 500 Kb from AT5G27060 pDRP |
| avrRpm1 | 5 | 23,536,891 | 0.066667 | Inside AT5GS8120 pDRP |
| avrRpt2 | 1 | 6,940,693 | 0.077778 | 10 Kb from AT1G20030 pathogenesis-related membrane protein. 500 Kb from AT1G17610 DRP |
| avrRpt2 | 1 | 6,992,858 | 0.066667 | 40 Kb from AT1G20030 pathogenesis-related membrane protein. 550 Kb from AT1G17610 DRP |
| avrRpt2 | 1 | 10,290,849 | 0.172 | 30 Kb from ERD2 protein transporter⇓. 900 Kb from AT1G27170, At1G27180 pDRPs. |
| avrRpt2 | 1 | 11,159,587 | 0.073333 | Inside AT1G31230, a protein required for amino acid synthesis ⇓.150 Kb from AT1G31540 pDRP. |
| avrRpt2 | 1 | 26,197,117 | 0.13 | 40 Kb of AT1G69550 pDRP |
| avrRpt2 | 2 | 17,656,278 | 0.134783 | ? |
| avrRpt2 | 3 | 4,140,699 | 0.077778 | 300 Kb from AT3G13650 disease resistance related protein. 500 Kb from NHL1 and NHL2 non-race specific disease resistance proteins |
| avrRpt2 | 3 | 16,553,416 | 0.073333 | 300 Kb from AT3G344670 pDRP. 500 Kb from AT3G44480 DRP. |
| avrRpt2 | 3 | 20,327,825 | 0.028571 | 100 Kb from AT3G55110 and AT3G55100 ABC trasporters⇑ |
| avrRpt2 | 4 | 9,577,993 | 0.126316 | 10 Kb from AT4G16990 pDRP ⇓.30 Kb from AT4G16950 DRP |
| avrRpt2 | 4 | 10,776,796 | 0.066667 | 20 Kb from AT4G19920 pDRP. 120 Kb from AT4G19530 pDRP⇓ |
| avrRpt2 | 4 | 13,221,777 | 0.066667 | 5 Kb from RPS2 (AT4G26090) R gene |
| avrRpt2 | 4 | 13,226,204 | 0 | Inside from RPS2 (AT4G26090) R gene |
| avrRpt2 | 4 | 13,753,481 | 0.0625 | 100 Kb from AT4G27220 pDRP. 200 Kb from RPS2 |
| avrRpt2 | 5 | 9,722,715 | 0.082353 | 20 Kb from AT5G27610 myb family transcription factor⇑ |
| avrRpt2 | 5 | 15,065,018 | 0.06875 | 330 Kb from AT5G38340 pDRP |

Table 2 above shows genetic loci with significant correlations to avr hypersensitive response traits (obtained using the conditional model with q<0.2). Nearby genes with known or putative rolls in the hypersensitive response traits are noted in the last column. Annotations are taken from the http://arabidopsis.com website. A question mark (?) indicates no significant annotations were found within 1 Mb. Abbreviations: (p)DRP, (putative) disease resistance protein; Up arrow (⇑)Down arrow (⇓),protein mRNA is significantly (at least two-fold change in expression level) up- or down-regulated during *P. syringae* infection.

Discussion of the Results and Other Work

The limitations of assuming that biological data are IID have been well documented in the area of genotype-phenotype association studies. Although standard population genetic models assume populations mate randomly, violations of this assumption result in latent population structure that inflates false positive rates an effect that will only increase as study sizes increase. There are two orthogonal approaches that are used to compensate for population structure. The more commonly used approach attempts to recalibrate standard statistics by normalizing results according to the distribution of the statistic across the entire genome. However, solutions to calibration are insufficient, as population structure also affects discriminatory power. The other approach assumes population structure is flat and can be captured by a small number of discrete (perhaps overlapping) clusters or continuums. Although these methods increase discriminatory power relative to simple IID models, there is mounting evidence that biological populations are hierarchically structured. For example, in addition to high level geographical/social constraints, structure exists within a number of subpopulations that have been studied. It stands to reason that, if hierarchical models describe the data better than flat cluster models, then such models will have higher discriminatory power. Aranzana et al. described one such model in their *Arabidopsis* study. As mentioned above, however, they found that their model was not calibrated and their data precluded a discriminatory power analysis.

Similar to the genotype-phenotype domain, early amino acid coevolution methods ignored the phylogenetic structure of the protein sequences, though it was later shown that phylogeny played a confounding roll. Similar to what happened in the population genetics field, a number of methods emerged that attempted to calibrate p-values based on global or local measures of average similarity or flat clusters based on early bifurcations of the phylogenetic tree. One approach that explicitly incorporates the phylogeny is the parametric bootstrap, in which standard IID models are recalibrated by generating independently evolved amino acids according to the single variable model. On the synthetic coevolution data (Example 1 above), this approach was too severe, resulting in overly conservative q-value estimates (see FIG. 4).

As was explained in more detail above, the results of the studies described herein show that evolutionary processes can confound association analyses and that generative models can correct for and, in fact, leverage the existence of these processes. Whereas traditional approaches have focused on calibrating significance metrics, the results described above show that explicitly modeling evolutionary processes increases discriminatory power and results in well-calibrated estimates of false positive rate.

The undirected joint model assumes that the two variables coevolve such that a mutation event in either variable elicits a corresponding change in the other variable. The conditional model assumes that a single variable is distributed according to the tree and is influenced by the predictor variable only at the tips of the tree. The directed joint model assumes that the variables coevolve, but the influence of one on the other is asymmetric. Of course, other evolutionary processes are possible. Neither the undirected joint nor conditional model outperformed the other on all real data sets, suggesting that both models should be considered when analyzing new data. Nonetheless, the conditional model better fit most of the real data that was analyzed. The conditional model better described the effects of immune pressure on HIV evolution and the correlation between HIV-1 p6 amino-acid pairs. This may be due to the rapid evolution of HIV and positive selection pressure from the immune response in conjunction with compensatory mutations in the observed patients.

A natural concern of any approach is the dependence of the method on external parameters. In the studies described above, the primary external parameter is the phylogenetic tree. Constructing an accurate phylogenetic tree can be problematic for reasons including recombination, non-independence among positions, and external selection pressure (such as immune pressure in the case of HIV evolution). Methods that incorporate these effects into tree learning are possible but usually come at a high computational cost. Fortunately, the results of the analyses using the generative models described above are not particularly sensitive to the precise structure of the phylogenetic tree. For instance, dozens of trees were generated for the Gag sequence data using a variety of methods. These methods included standard tree building methods (PHYML and DNAML from the PHYLIP package) using every possible parameter setting. Although the structure of the tree differed rather substantially according to the maximum branch-score distance (which is roughly the root mean squared difference in evolutionary distance between two sequences), the differences in associations at the $q<0.2$ cutoff were negligible.

The examples above are focused on the correlation of discrete (specifically binary) variables. Generalization to multi-state variables is straightforward, although may suffer a loss in power. The models also can be generalized to continuous and/or discrete predictor and target variables and to situations with multiple predictor and target variables, thus producing a directed network (acyclic or otherwise) of relationships among multiple variables. Potential applications of multiple predictor variables include learning the combined effects of drug and immune pressure on HIV evolution, identifying chains of compensatory mutations, learning the influence of diploid genes on phenotype and learning networks of interacting genes and proteins.

The problem of population structure confounding association studies is a ubiquitous problem across many biological disciplines. Existing solutions vary across these disciplines, but typically focus on correcting for shared population structure. However, population structure in either variable can lead to loss of discriminatory power and poor statistical calibration using the existing solutions. The flexibility and intuitive nature of generative models makes these models a powerful choice for dealing with a variety of biological processes.

Figure 9:
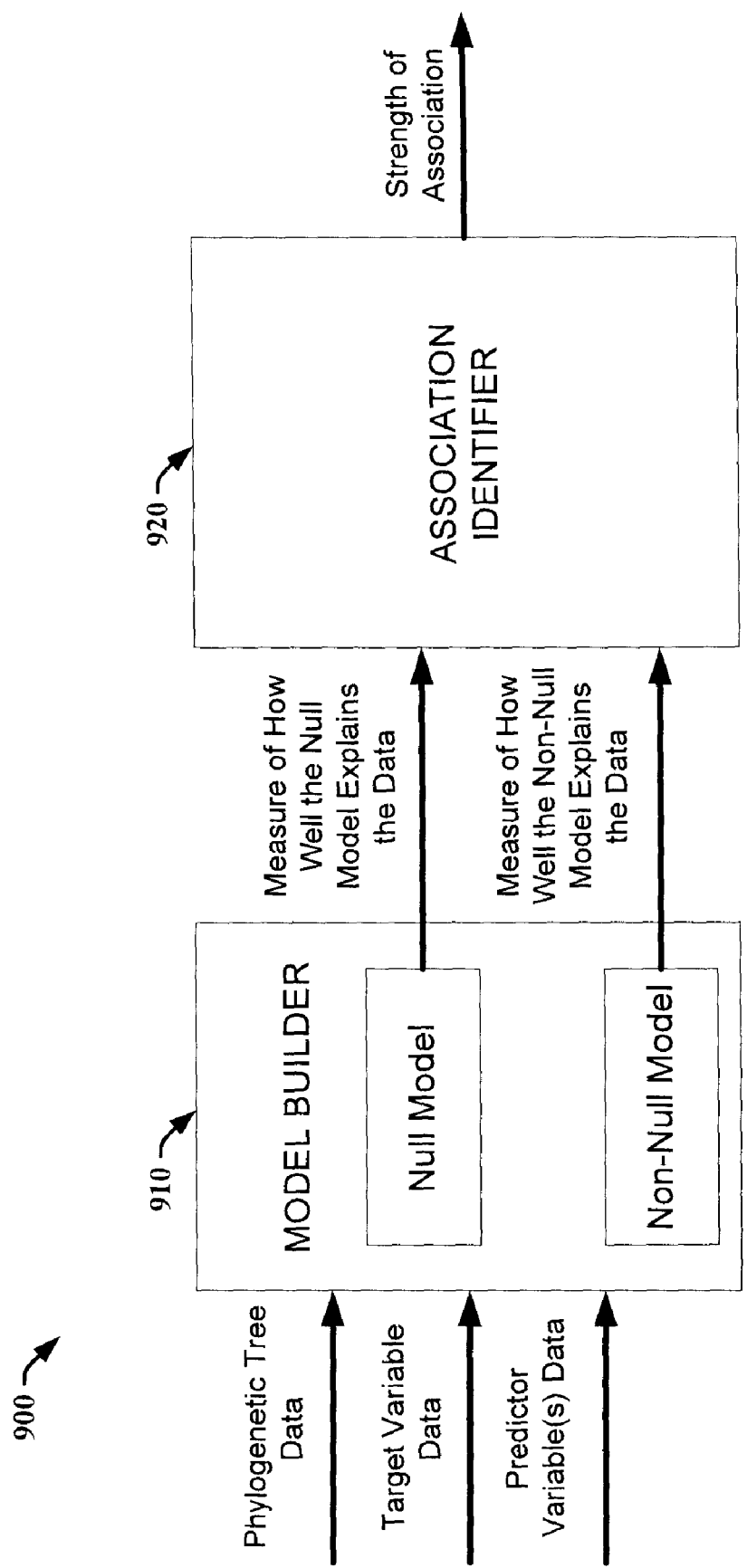
FIG. 9 is a block diagram of one example of a system for identifying associations.

FIG. 9 schematically illustrates one example of a system 900 for identifying associations between variables. The system 900 includes a model builder 910 and an association identifier 920. The components 910 and 920 can be implemented by software or combinations of software and hardware and can be the same process executing on a single or a plurality of computers or multiple processes executing on a single or a plurality of computers.

The model builder can be configured to receive data and to build models for each of one or more target variables. The data to be received can relate to observations about the one or more target variables and one or more predictor variables across a set of instances and a phylogenetic tree (e.g., topology and branch length). By way of example, the model builder 910 can build a null directed acyclic graphical (DAG) model based on the assumption that a target variable evolves according to the phylogenetic tree and a non-null directed acyclic graphical (DAG) model based on the assumption that the target variable evolves according to the phylogenetic tree and is influenced by one or more predictor variables at the tips of the phylogenetic tree. The model builder 910 can build the DAG models, for instance, at least in part by adjusting a stationary distribution parameter and an evolutionary rate parameter of a continuous time Markov process to maximize the likelihood of the observed data.

Figure 10:
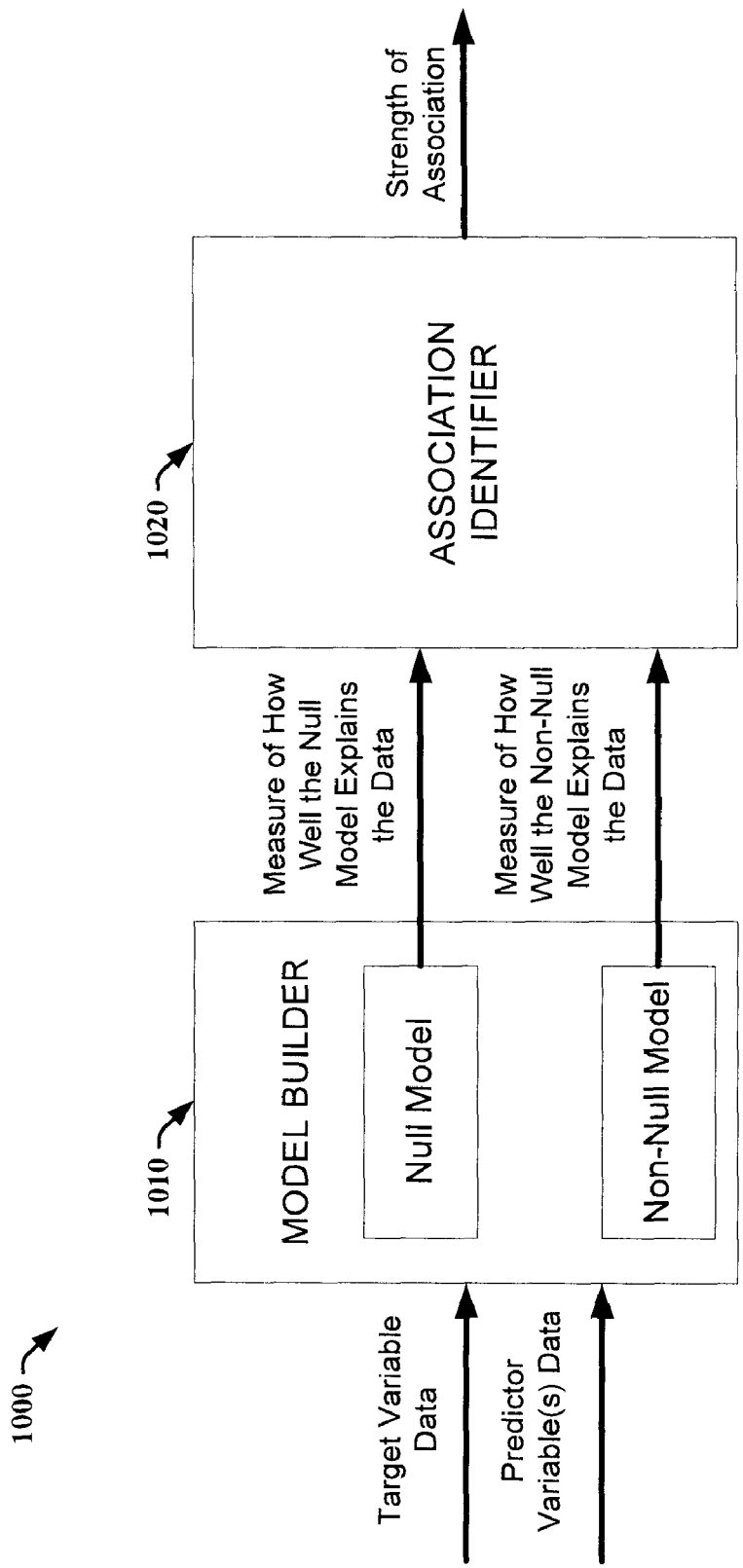
FIG. 10 is a block diagram of another example of a system for identifying associations.

By way of another example, the model builder 910 can build a null directed acyclic graphical (DAG) model based on the assumption that a target variable and a predictor variable evolve independently according to the phylogenetic tree and a non-null directed acyclic graphical (DAG) model based on the assumption that the target variable and the predictor variable coevolve along the phylogenetic tree and that the predictor variable influences evolution of the target variable but that the target variable does not influence evolution of the variable. By way of yet another example, as shown in FIG. 10, instead of receiving data relating to a phylogenetic tree, the model builder 1010 can build a null directed acyclic graphical (DAG) model and a non-null directed acyclic graphical (DAG) model by searching over phylogenetic tree structures, parameters of those phylogenetic tree structures and parameters relating to the influence of the one or more predictor variables on the target variable to identify one or more phylogenetic tree structures that explain the data well.

The model builders 910, 1010 can be configured to receive any suitable type of data including but not limited to biological, pathophysiological, physiological, medical and/or otherwise health-related data. The data can be, for example, information relating to genes, nucleotides, proteins, peptides, amino acids, phenotypes, diseases, medical conditions, etc. The data can be discrete, continuous, binary, multistate and mixtures thereof. For instance, the target variable can be a continuous variable that is a linear regression of the one or more predictor variables or a discrete variable that is a logistic regression of the one or more predictor variables. The target variable can, for example, relate to a phenotype and at least one of the one or more predictor variables can relate to a genotype. Alternatively, the target variable can relate to a genotype and at least one of the one or more predictor variables can relate to a phenotype.

The association identifiers 920, 1020 can be configured to assess the strength of the association between the target variable and the one or more predictor variables. The association identifiers 920, 1020 can assess the strength of association between the target variable and the one or more predictor variables by determining how much the non-null DAG model better explains the observed data than the null DAG model. The association identifiers 920, 1020 can assess the strength of association at least in part by employing a Bayesian criterion of model posterior probability, Bayesian information criterion, a likelihood ratio and/or cross validation. The association identifiers 920, 1020 optionally can compute false discovery rates (FDR) and/or q-values from a likelihood ratio statistic to adjust for multiple comparisons.

The systems 900, 1000 are useful for understanding whether two or more variables are correlated with each other. Examples of such uses include the study of coevolving protein residues, genotype-phenotype associations and external evolutionary influences on phenotype (e.g. HLA-driven escape mutations). In complex disease studies, for instance, the systems 900, 1000 can be used to scan genetic markers to identify genotypes that may play a causal role in a disease or phenotype of interest. The systems 900, 1000 can be used to develop treatments, for instance, by employing the identified associations to identify epitopes and develop vaccines (e.g., as described in U.S. patent application Ser. Nos. 11/324,634 and 11/324,467).

The systems described above can be implemented on a network, in whole or in part, by electromagnetic signals. These manufactured signals can be of any suitable type and can be conveyed on any type of network. For instance, the systems can be implemented by electronic signals propagating on electronic networks, such as the Internet. Wireless communications techniques and infrastructures also can be utilized to implement the systems.

As used in this application, the term "component" is intended to refer to a computer-related entity, either hardware, a combination of hardware and software, software, or software in execution. For example, a component can be, but is not limited to, a process running on a processor, a processor, an object, an executable, a thread of execution, a program, and a computer. By way of illustration, an application running on a server and/or the server can be a component. In addition, a component can include one or more subcomponents. One or more components can reside within a process and/or thread of execution and a component can be localized on one computer and/or distributed between two or more computers.

Figure 11:
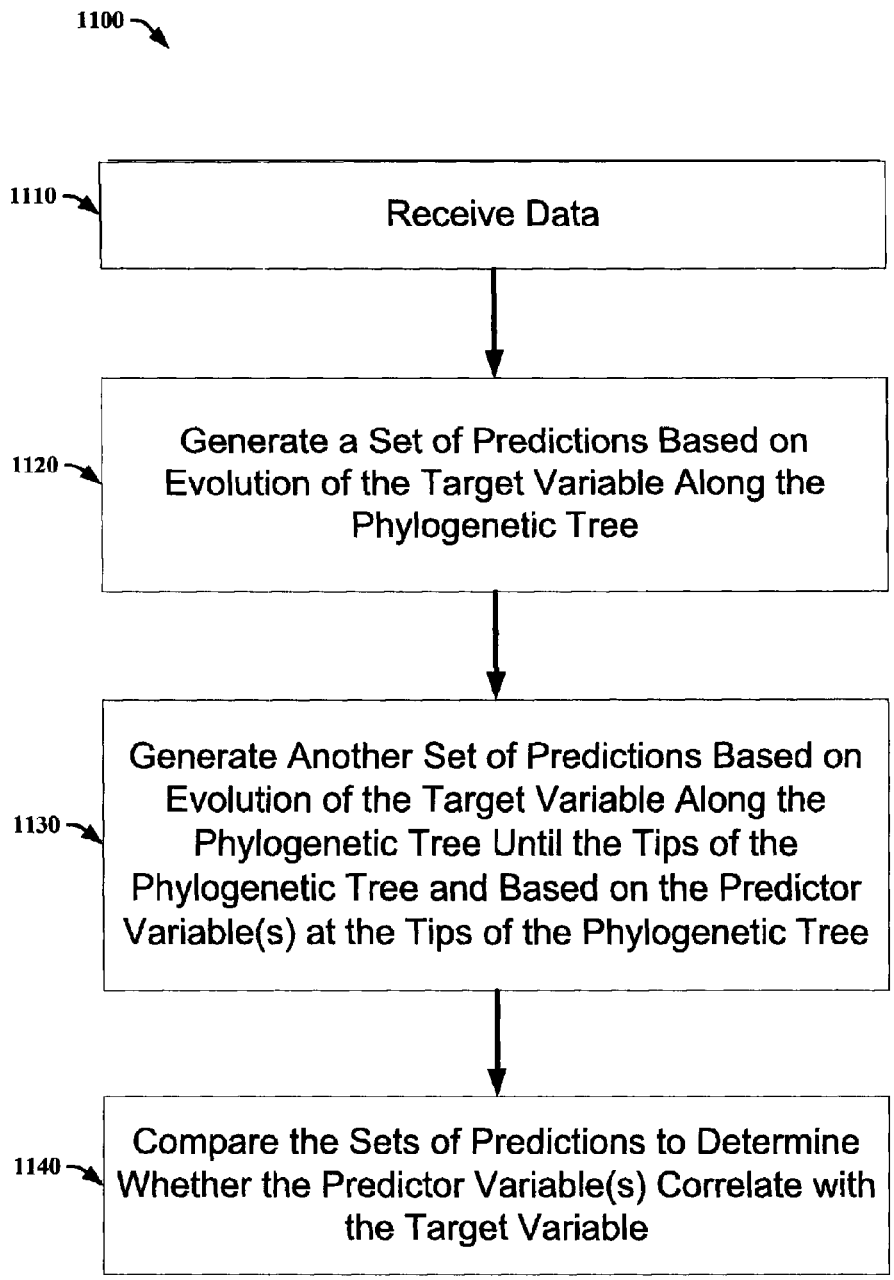
FIG. 11 is a flowchart representing one example of a method of identifying associations.

FIG. 11 is a flowchart representing a method 1100 of identifying correlations. The method 1100 can be performed by computer-executable instructions, for instance, transmitted by a manufactured signal or stored on one or more computer-readable media, to generate correlations. At step 1110, data relating to one or more predictor variables and a target variable across a set of instances and data relating to a phylogenetic tree is received. The data can be any suitable type of data including but not limited to biological, pathophysiological, physiological, medical and/or otherwise health-related data. The data can be, for example, information relating to genes, nucleotides, proteins, peptides, amino acids, phenotypes, diseases, medical conditions, etc. The data can be discrete, continuous, binary, multistate and mixtures thereof. For instance, the target variable can be a continuous variable that is a linear regression of the one or more predictor variables or a discrete variable that is a logistic regression of the one or more predictor variables.

Figure 12:
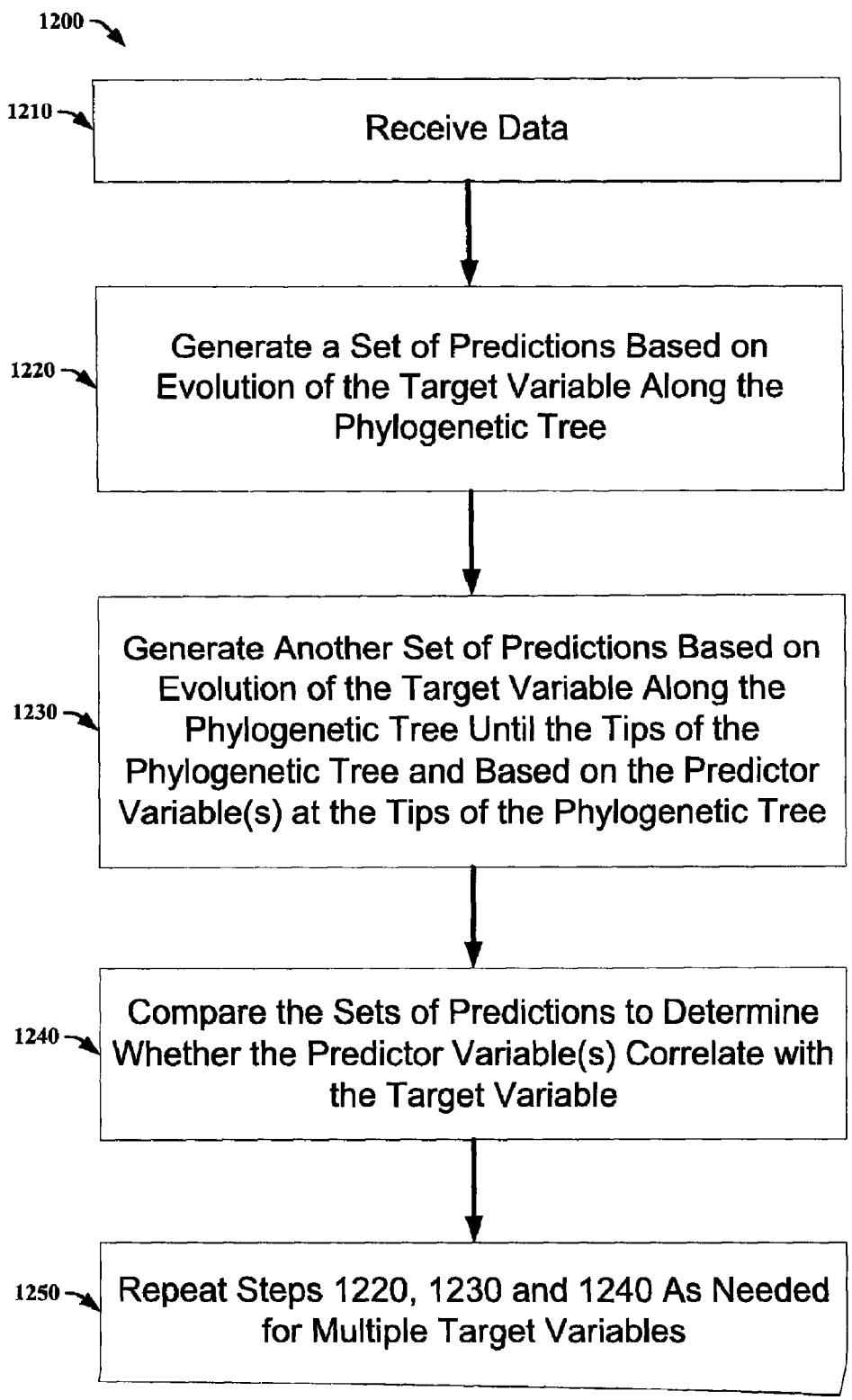
FIG. 12 is a flowchart representing another example of a method of identifying associations.

A set of predictions based on the evolution of the target variable along the phylogenetic tree can be generated at step 1120 and another set of predictions based on the evolution of the target variable along the phylogenetic tree until the tips of the phylogenetic tree and based on the one or more predictor variables at the tips of the phylogenetic tree can be generated at 1130. The sets of predictions can be compared at step 1140 to determine whether the one or more predictor variables correlate with the target variable. As shown in FIG. 12, the steps of generating 1220, 1230 and comparing 1240 can be performed any suitable number of times when data for a plurality of target variables is received.

The correlations determined via the method 1100 can be employed to facilitate developing a treatment such as a vaccine (e.g., as described in U.S. patent application Ser. Nos. 11/324,634 and 11/324,467). By way of example, if the target variable is an HIV sequence, the correlations can be used to develop an AIDS vaccine. Genome wide association studies can be facilitated by performing the methods 1100, 1200, for instance, if the target variable(s) is a phenotype (or genotype) and at least one of the one or more predictor variables is a genotype (or phenotype). The correlations so determined can be used to develop, for instance, a genetic therapy. By way of another example, if the variables are amino acid sequences, the methods 1100, 1200 can be used to facilitate predicting protein structures (e.g., see Pollock et al.). These predicted protein structures can be used to develop, for instance, protein based treatments such as a protein receptor treatment, a protein ligand treatment and/or a protein receptor inhibitor treatment. Other examples of protein based treatments include molecules that up or down regulate a gene product.

Figure 13:
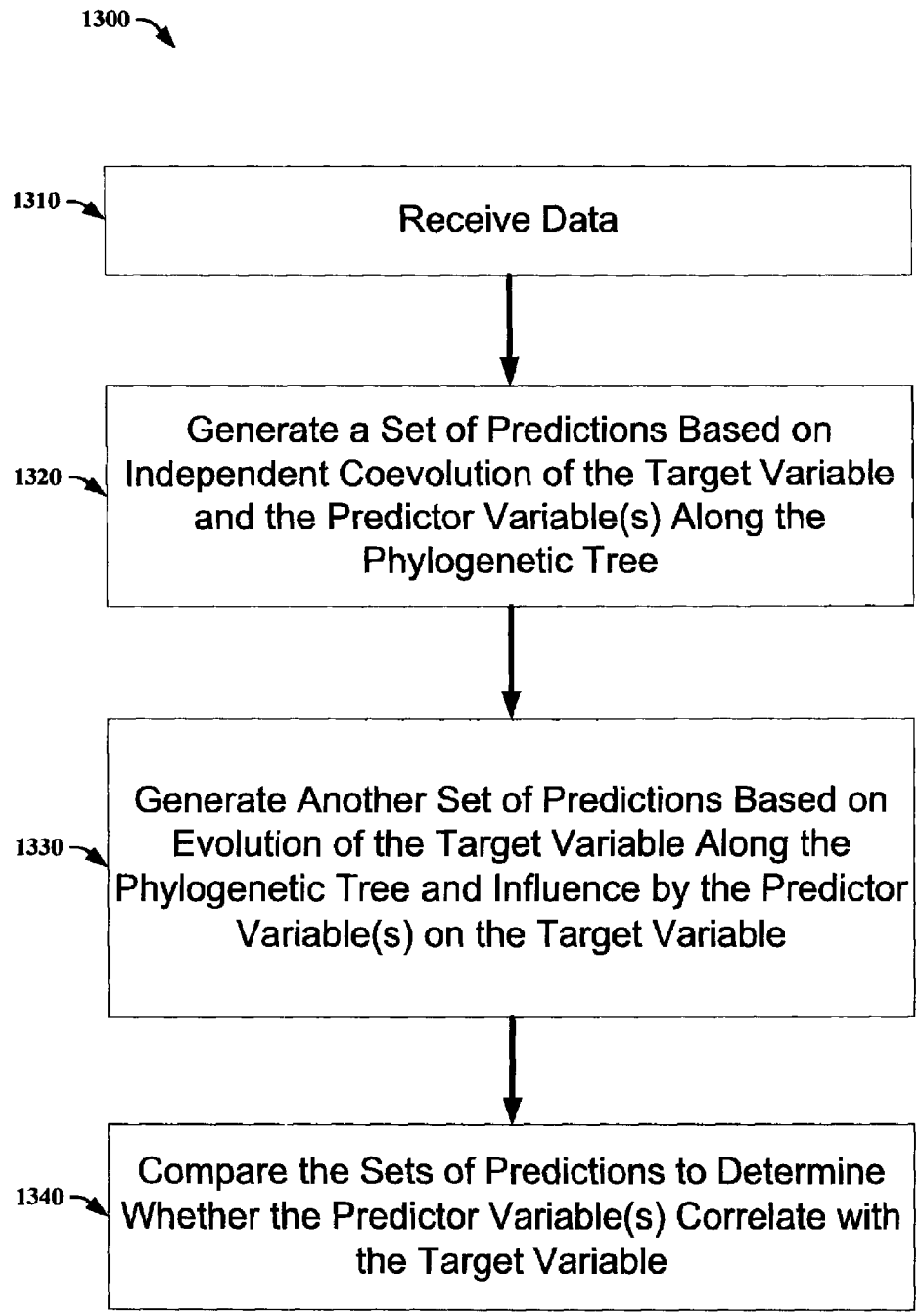
FIG. 13 is a flowchart representing another example of a method of identifying associations.

FIG. 13 is a flowchart that represents a method 1300 to generate correlations. The method 1300 can be performed by for instance, computer-executable instructions. At step 1310, data relating to one or more predictor variables and a target variable across a set of instances and data relating to a phylogenetic tree can be received. The data can be used to generate 1320 a set of predictions based on independent coevolution of the one or more predictor variables and the target variable along the phylogenetic tree. The data also can be used to generate 1330 another set of predictions based on evolution of the one or more predictor variables along the phylogenetic tree and evolution of the target variable along the phylogenetic tree dependent upon the one or more predictor variables. At step 1340, the sets of predictions can be compared to determine whether the one or more predictor variables correlate with the target variable. The computer-executable instructions can be, for instance, transmitted by a manufactured signal or stored on one or more computer-readable media.

The method 1300 can be used to facilitate developing a treatment. For instance, at least some of the determined correlations can be used to develop a vaccine, such as a vaccine against HIV. Other examples of treatments that can be developed by employing the method 1300 include those described above (e.g., protein based treatments, genetic treatments, gene product regulators, etc.). The method 1300 also can be used to study protein structures.

Figure 14:
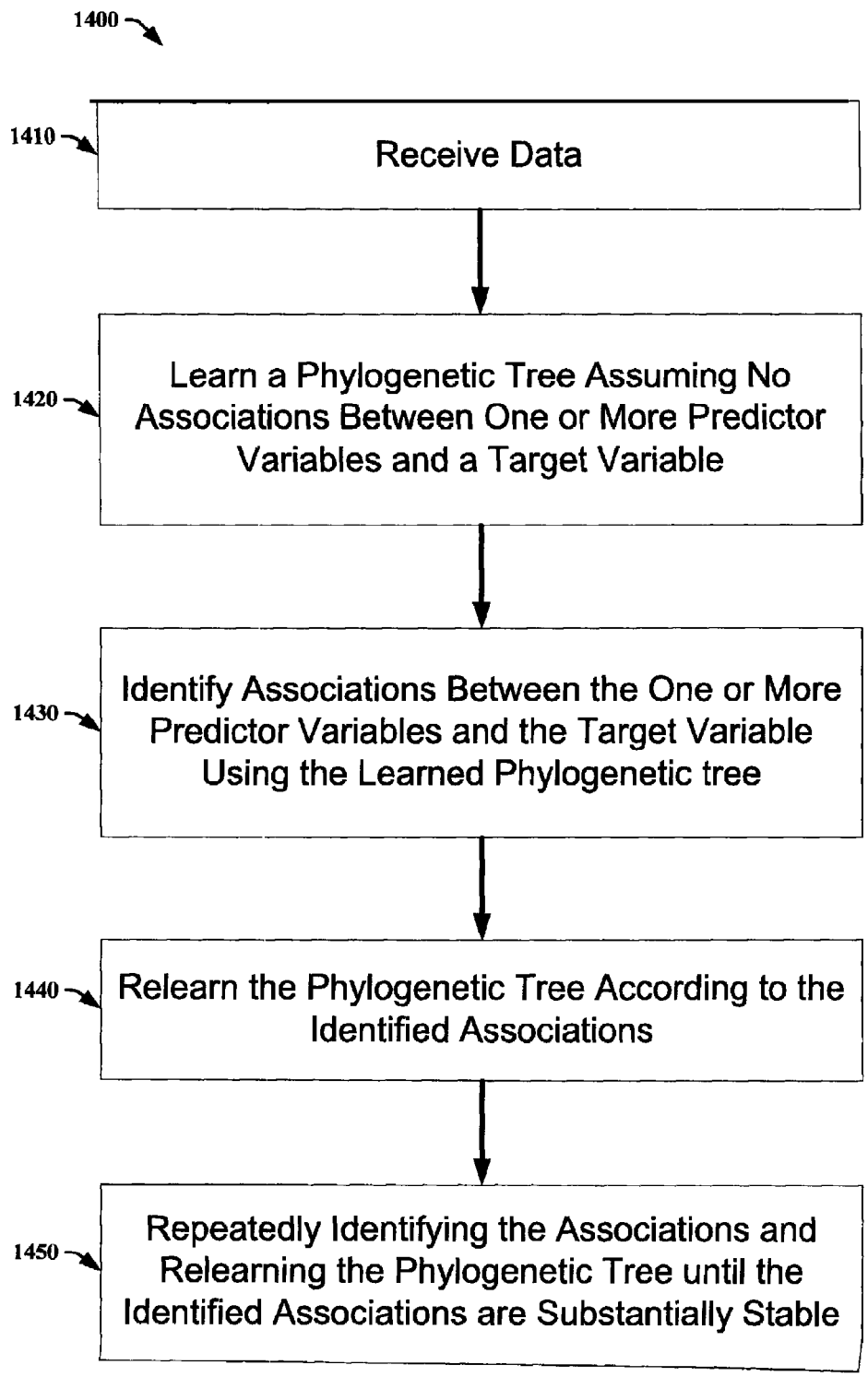
FIG. 14 is a flowchart representing yet another example of a method of identifying associations.

FIG. 14 is a flowchart representing a method 1400 of simultaneously inferring a phylogenetic tree and identifying associations among predictor and target variables. The method 1400 can be transmitted by manufactured signals and/or stored on one or more computer-readable media, for instance. As shown at step 1410, data relating to one or more predictor variables and a target variable across a set of instances can be received. Assuming no associations between the one or more predictor variables and the target variable, a phylogenetic tree can be learned from the data at step 1420 and at step 1430, associations between the one or more predictor variables and the target variable using the learned phylogenetic tree can be identified, for instance using any of the methods/systems described above (e.g., conditional, joint directed). At step 1440, the phylogenetic tree can be relearned according to the identified associations. The associations can be repeatedly identified and the phylogenetic tree relearned 1450 until the identified associations are substantially stable. The associations between the one or more predictor variables and the target variable can be identified in any suitable manner, such as those described above (e.g., using a Bayesian cutoff for relevance and/or a frequentist cutoff for relevance).

The methods described above can be implemented by computer-executable instructions stored on computer-readable media or conveyed by a signal of any suitable type. The methods can be implemented at least in part manually. The steps of the methods can be implemented by software or combinations of software and hardware and in any of the ways described above. The computer-executable instructions can be the same process executing on a single or a plurality of computers or multiple processes executing on a single or a plurality of computers. The methods can be repeated any number of times as needed and the steps of the methods can be performed in any suitable order.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules can be combined or distributed as desired. Although the description above relates generally to computer-executable instructions of a computer program that runs on a computer and/or computers, the user interfaces, methods and systems also can be implemented in combination with other program modules. Generally, program modules include routines, programs, components, data structures, etc. that perform particular tasks and/or implement particular abstract data types.

Moreover, the methods and systems described herein can be practiced with all suitable computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules can be located in both local and remote memory storage devices. The methods and systems described herein can be embodied on a computer-readable medium having computer-executable instructions as well as signals (e.g., electronic signals) manufactured to transmit such information, for instance, on a network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing some of the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature can be combined with one or more other features of the other implementations of the subject matter as may be desired and advantageous for any given or particular application.

In regard to the various functions performed by the above described components, computer-executable instructions, means, systems and the like, the terms are intended to correspond, unless otherwise indicated, to any functional equivalents even though the functional equivalents are not structurally equivalent to the disclosed structures. Furthermore, to the extent that the terms "includes," and "including" and variants thereof are used in either the specification or the claims, these terms are intended to be inclusive in a manner the same as the term "comprising." Accordingly, the claimed subject matter is intended to embrace all such alterations, modifications, and variations that fall within the spirit and scope of the appended claims.

What is claimed is:

1. A system for identifying associations between variables, the system stored on one or more computer-readable media, the system comprising: one or more processors;

memory coupled to the one or more processors, the memory comprising:

a model builder configured for each of one or more target variables to:
receive:
observed data relating to the target variable and one or more predictor variables across a set of instances; and data relating to a phylogenetic tree; and
build:
a null directed acyclic graphical (DAG) model, wherein the target variable evolves downstream from the root nodes to the tips of the phylogenetic tree; and
a non-null directed acyclic graphical (DAG) model, wherein the target variable evolves downstream from the root nodes to the tips of the phylogenetic tree and the target variables at the tips of the phylogenetic tree are influenced by the one or more predictor variables but the target variables are not influenced at other portions of the phylogenetic tree; and
an association identifier configured to assess a strength of association between the target variable and the one or more predictor variables by determining how much the non-null DAG model better explains the observed data than the null DAG model.

2. The system of claim 1, wherein the association identifier is configured to assess the strength of association at least in part by employing a Bayesian criterion of model posterior probability.

3. The system of claim 1, wherein the association identifier is configured to assess the strength of association at least in part by employing a Bayesian information criterion (BIC).

4. The system of claim 1, wherein the association identifier is configured to assess the strength of association at least in part by employing a likelihood ratio test.

5. The system of claim 1, wherein the association identifier is configured to compute false discovery rates (FDR) and/or q-values from a likelihood ratio statistic to adjust for multiple comparisons.

6. The system of claim 1, wherein the association identifier is configured to assess the strength of association at least in part by employing cross validation.

7. The system of claim 1, wherein the target variable is a continuous variable.

8. The system of claim 1, wherein the target variable is a continuous variable that is a linear regression of the one or more predictor variables relating to the target variable.

9. The system of claim 1, wherein at least one of the one or more predictor variables is a continuous variable.

10. The system of claim 1, wherein the target variable is a discrete variable that is a logistic regression of the one or more predictor variables relating to the target variable.

11. The system of claim 1, wherein the target variable relates to a phenotype and at least one of the one or more predictor variables relates to a genotype.

12. The system of claim 1, wherein the target variable relates to a genotype and at least one of the one or more predictor variables relates to a phenotype.

13. The system of claim 1, wherein the target variable relates to amino acid sequences.

14. The system of claim 1, wherein the target variable and at least one of the one or more predictor variables relate to amino acid sequences.

15. A system for identifying associations between variables, the system stored on one or more computer-readable media, the system comprising:
one or more processors;
memory coupled to the one or more processors, the memory comprising:
a model builder configured to:
receive:
observed data relating to:
a target variable across a set of instances; and one or more predictor variables across the set of instances; and
data relating to a phylogenetic tree and build:
a null directed acyclic graphical (DAG) model, wherein the target variable and the predictor variable evolve independently according to the phylogenetic tree; and
a non-null directed acyclic graphical (DAG) model, wherein the target variable and the predictor variable coevolve down the phylogenetic tree, the predictor variable influences evolution of the target variable but the target variable does not influence evolution of the predictor variable, and the target variable evolves with a first rate when the predictor variable is present and evolves with a second rate when the predictor variable is absent; and
an association identifier configured to assess a strength of association between the target variable and the one or more predictor variables by determining how much the non-null DAG model better explains the observed data than the null DAG model.

16. The system of claim 15, wherein the target variable relates to a phenotype and the predictor variable relates to a genotype.

17. The system of claim 15, wherein the target variable relates to a genotype and the predictor variable relates to a phenotype.

18. The system of claim 15, wherein the target variable relates to amino acid sequences.

19. The system of claim 15, wherein the predictor variable relates to amino acid sequences.

* * * * *